(12) United States Patent
Sukumaran et al.

(10) Patent No.: US 12,215,197 B2
(45) Date of Patent: Feb. 4, 2025

(54) CRYSTALLINE, TWO DIMENSIONAL POLYMERS AND A PROCESS FOR THE PREPARATION THEREOF

(71) Applicant: COUNCIL OF SCIENTIFIC AND INDUSTRIAL RESEARCH, New Delhi (IN)

(72) Inventors: Santhosh Babu Sukumaran, Pune (IN); Karayamkodath Chandran Ranjeesh, Pune (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 664 days.

(21) Appl. No.: 17/600,955

(22) PCT Filed: Apr. 2, 2020

(86) PCT No.: PCT/IN2020/050320
§ 371 (c)(1),
(2) Date: Oct. 1, 2021

(87) PCT Pub. No.: WO2020/202213
PCT Pub. Date: Oct. 8, 2020

(65) Prior Publication Data
US 2022/0185963 A1 Jun. 16, 2022

(30) Foreign Application Priority Data
Apr. 3, 2019 (IN) .............................. 201911013442

(51) Int. Cl.
*C08G 73/18* (2006.01)
*C07C 17/02* (2006.01)
*C07C 51/09* (2006.01)
*C07C 67/347* (2006.01)
*C07D 235/16* (2006.01)

(52) U.S. Cl.
CPC .............. *C08G 73/18* (2013.01); *C07C 17/02* (2013.01); *C07C 51/09* (2013.01); *C07C 67/347* (2013.01); *C07D 235/16* (2013.01)

(58) Field of Classification Search
USPC ........................................................ 528/423
See application file for complete search history.

(56) References Cited

FOREIGN PATENT DOCUMENTS

| KR | 20120001559 A | 1/2012 |
|---|---|---|
| KR | 101218567 B1 | 1/2013 |

OTHER PUBLICATIONS

International Search Report; International Application No. PCT/IN2020/050320; International Filing Date—Apr. 2, 2020; Date of Mailing- Aug. 10, 2020; 4 pages.
Jiang et al., "Band Gap Engineering In Fluorescent Conjugated Microporous Polymers", 2011, Chemical Science, vol. 2, (No. 9), pp. 1777-1781.
Kim et al., "Polybenzimidazole Bearing Benzimidazolyl Pendants: Synthesis And Proton Conductivity", Bulletin of the Korean Chemical Society, 2010, vol. 31, (No. 5), pp. 1411-1414.
Rabbani et al., "Pyrene-Directed Growth Of Nanoporous Benzimidazole-Linked Nanofibers And Their Application To Selective CO2 Capture And Separation," Journal of Materials Chemistry, 2012, vol. 22, (No. 48), pp. 25409-25417.
Stylianou et al. "A Guest-Responsive Fluorescent 3D Microporous Metal Organic Framework Derived From A Long-Lifetime Pyrene Core," Journal Of The American Chemical Society, 2010, vol. 132, (No. 12), pp. 4119-4130.
Written Opinion for International Application No. PCT/IN2020/050320; International Filing Date—Apr. 2, 2020; Date of Issue—Aug. 10, 2020; 7 pages.

*Primary Examiner* — Terressa Boykin
(74) *Attorney, Agent, or Firm* — CANTOR COLBURN LLP

(57) ABSTRACT

The present invention relates to a crystalline, two dimensional polymer of Formula I and a process for the preparation thereof.

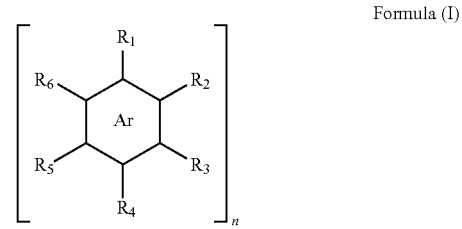

Formula (I)

10 Claims, 8 Drawing Sheets

CRYSTALLINE, TWO DIMENSIONAL POLYMERS AND A PROCESS FOR THE PREPARATION THEREOF

CROSS REFERENCE TO RELATED APPLICATIONS

This application is a National Stage application of PCT/IN2020/050320, filed Apr. 2, 2020, which claims priority to India Application No. 201911013442, filed Apr. 3, 2019, the contents of which are incorporated by reference in their entirety.

FIELD OF THE INVENTION

The present invention relates to a crystalline, two dimensional polymers of Formula I and a process for the preparation thereof.

BACKGROUND AND PRIOR ART OF THE INVENTION

COFs (Covalent Organic Frameworks) are unique 2D-platform for proton conduction (key factor in Fuel cells). Upon doping with imidazole or phosphoric acid however, due to weak host guest interactions, the leaching of proton carriers from the channels is unavoidable, if used under harsh conditions such as high humidity and high temperatures. The uniform doping of imidazole molecules in the 2D-dimensional framework and thereby the real mechanistic understanding is challenging, these materials invite serious challenges towards commercialization.

Article titled "Phosphoric acid loaded Azo (—N═N—) based Covalent Organic Framework for proton conduction" by Rahul Banerjee et al. published in Journal of American Chemical Society, 2014, 136 (18), pp 6570-6573 reports two new chemically stable functional crystalline covalent organic frameworks (COFs) (Tp-Azo and Tp-Stb) that were synthesized using the Schiff base reaction between triformylphloroglucinol (Tp) and 4,4'-azodianiline (Azo) or 4,4'-diaminostilbene (Stb), respectively. Both COFs show the expected keto-enamine form, and high stability toward boiling water, strong acidic, and basic media. $H_3PO_4$ doping in Tp-Azo leads to immobilization of the acid within the porous framework, which facilitates proton conduction in both the hydrous ($\sigma=9.9\times10^{-4}$ S cm$^{-1}$) and anhydrous state ($\sigma=6.7\times10^{-5}$ S cm$^{-1}$). This report constitutes the first emergence of COFs as proton conducting materials.

Article titled "Pyrene-directed growth of nanoporous benzimidazole-linked nanofibers and their application to selective CO2 capture and separation" by H. M. El-Kaderi et al. published in Journal of Material Chemistry, 2012, 22, 25409-25417 reports that a pyrene-based benzimidazole-linked polymer (BILP-10) has been synthesized by the co-condensation of 1,3,6,8-tetrakis(4-formylphenyl)pyrene and 1,2,4,5-benzenetetramine tetrahydrochloride in dimethyl formamide. The use of pyrene as a molecular building unit leads to the formation of self-assembled nanofibers that have moderate surface area (SABET=787 m$^2$ g$^{-1}$) and very high $CO_2/N_2$ (128) and $CO_2/CH_4$ (18) selectivities at 273 K. Furthermore, results from gas uptake measurements indicate that BILP-10 can store significant amounts of $CO_2$ (4.0 mmol at 273 K/1.0 bar) and $H_2$ (1.6 wt % at 77 K/1.0 bar) with respective isosteric heats of adsorption of 38.2 and 9.3 kJ mol$^{-1}$ which exceed all of the previously reported values for BILPs and are among the highest values reported to date for unmodified porous organic polymers. The polymer has no long range ordering, evident from PXRD which lacks any sharp peak in the PXRD. It suggests polymerization may proceed by kinetically driven imine formation followed by cyclisation to the imidazole in a non-uniform rate. It is clear from the PXRD analysis of BIP-1, new synthetic route helps to undergo thermodynamically controlled reversible condensation reaction of the monomers, in turn which results in a crystalline framework.

There is need to explore a new synthetic route to prepare imidazole linked pyrene based crystalline 2D-polymer for proton conducting application.

OBJECTIVES OF THE INVENTION

Main objective of the present invention is to provide a crystalline, two dimensional polymer of Formula (I).

Another objective of the present invention is to provide a process for the preparation of the crystalline, two dimensional polymers of Formula (I).

SUMMARY OF THE INVENTION

Accordingly, the present invention provides a crystalline, two dimensional polymer of Formula (I),

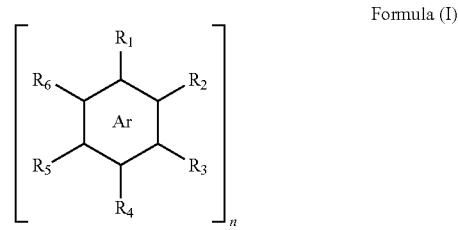

Formula (I)

wherein $R_1$ to $R_6$ are same or different and independently selected from hydrogen, alkyl, substituted or unsubstituted alkyl, substituted or unsubstituted aryl, heteroalkyl or heteroaryl; n is the number of repeating units of the polymer and Ar is aromatic ring.

The crystalline, two dimensional polymer of Formula (I) is selected from BIP-1, BIP-2 or BIP-3.

In an embodiment, the present invention provides a process for the preparation of the crystalline, two dimensional polymers of Formula (I) comprising the steps of:

a) adding halogen to pyrene in a solvent at a temperature ranging from 25° C. to 30° C. to obtain a reaction mixture followed by stirring the reaction mixture at a temperature in the range of 100 to 150° C. for a time period in the range of 2 to 5 hours to obtain 1,3,6,8-tetrahalopyrene;

b) charging a mixture of boronic acid, 1,3,6,8-tetrahalopyrene of step (a), palladium catalyst, and a base in a solvent at a temperature in the range of 100 to 150° C. for a time period in the range of 60 to 80 hours to obtain 1,3,6,8-tetrakis(4-(methoxycarbonyl)phenyl) pyrene;

c) heating a mixture of 1,3,6,8-tetrakis(4-(methoxycarbonyl)phenyl)pyrene of step (b), and a base in a solvent at a temperature in the range of 60 to 80° C. for a time period in the range of 8 to 10 hours followed by drying the solvent to obtain residue;

d) adding water into the residue of step (c) followed by stirring at a temperature in the range of 25° C. to 30° C. for a time period in the range of 1 to 3 hours and adjusting the pH in the range of 1 to 2 to obtain 1, 3, 6, 8-tetrakis (p-benzoic acid) pyrene;

e) charging a mixture of 1,3,6,8-tetrakis(p-benzoic acid) pyrene of step (d), 1,2,4,5-benzenetetramine tetrahydrochloride and a catalyst in a solvent at a temperature in the range of 120° C. to 160° C. for a time period in the range of 45 to 48 hours to obtain a solution and continuing stirring at a temperature in the range of 180° C. to 200° C. for a time period in the range of 45 to 48 hours followed by adjusting pH of the solution to 8-9 to obtain the polymer;

wherein the polymer is Benzimidazole-linked two dimensional polymer.

DETAILED DESCRIPTION OF THE INVENTION

Figure 1:
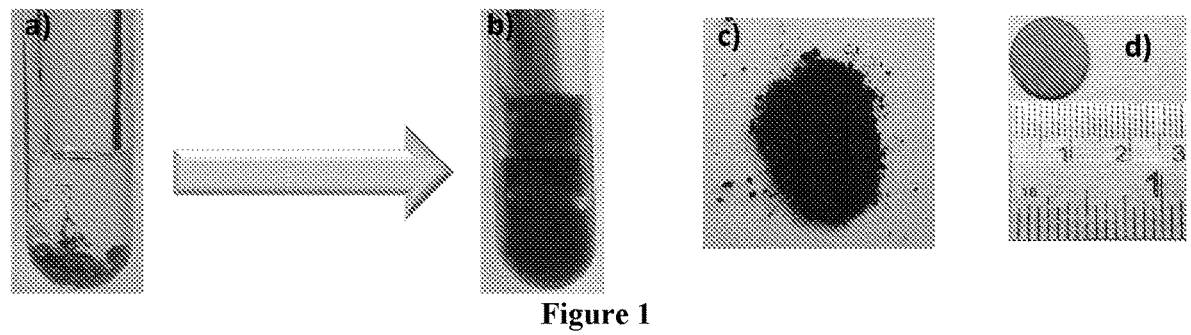
FIG. 1: A) Before polymerization of BIP-1; B) After polymerization of BIP-1; C) Isolated yield; D) BIP-1 pellet

The invention will now be described in detail in connection with certain preferred and optional embodiments, so that various aspects thereof may be more fully understood and appreciated.

The present invention provides a crystalline, two dimensional polymer of Formula I and a process for the preparation thereof.

In an embodiment, the present invention provides a crystalline, two dimensional polymer of Formula I;

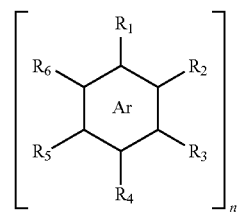

Formula (I)

wherein $R_1$ to $R_6$ are same or different and independently selected from hydrogen, alkyl, substituted or unsubstituted alkyl, substituted or unsubstituted aryl, heteroalkyl or heteroaryl; wherein n is the number of repeating units of the polymer and n is in the range of 3 to 6 but not 4; and wherein Ar is an aromatic ring.

In preferred embodiment, the present invention provides a crystalline, two dimensional polymer of Formula (I),

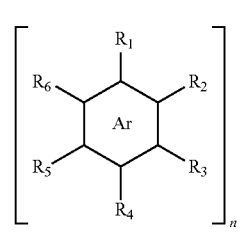

Formula (I)

wherein $R_1$ to $R_6$ are same or different and independently selected from hydrogen,

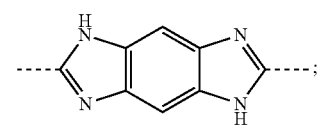

wherein Ar is selected from

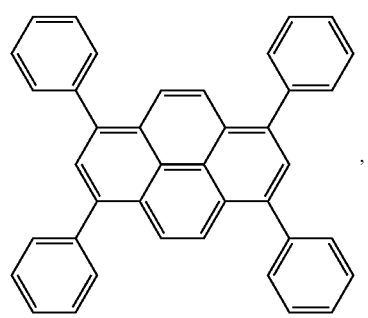

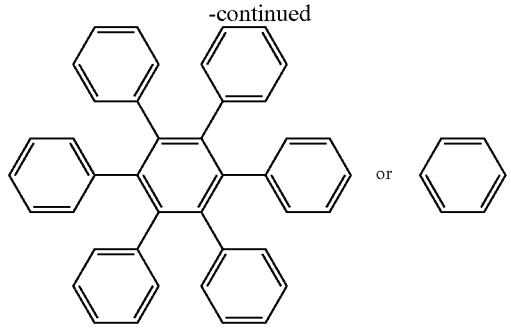
or
n is the number of repeating units of the polymer.
The crystalline, two dimensional polymer of Formula (I) is selected from BIP-1, BIP-2 or BIP-3; having formula as:
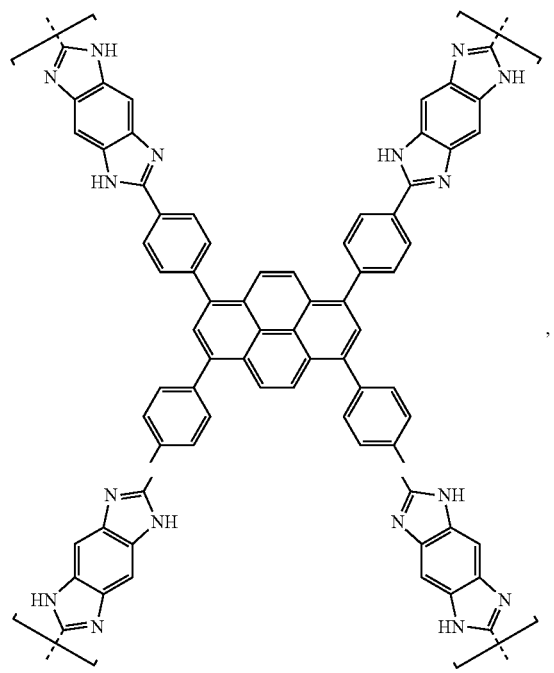
BIP-1

-continued

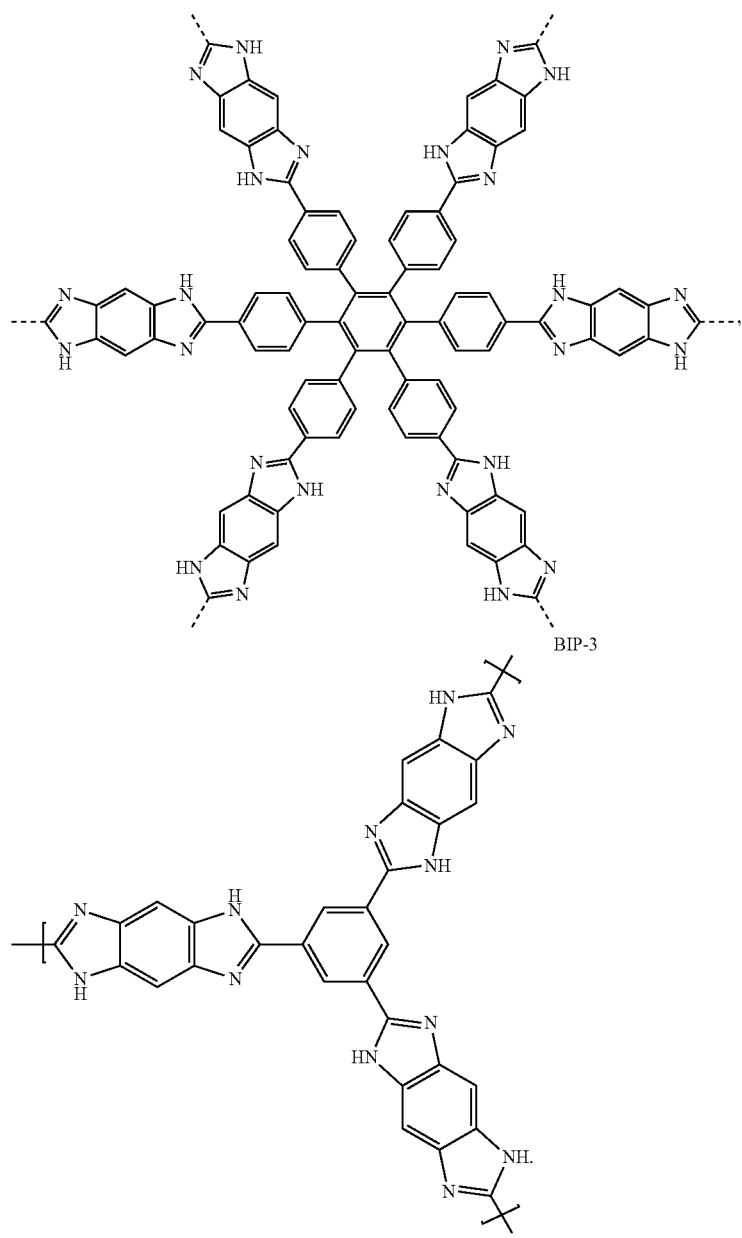

BIP-2

BIP-3

In another embodiment, the present invention provides a crystalline, two dimensional polymer of Formula I, wherein n is the number of benzimidazole units in the polymer, and n is 3-6, but not 4, wherein the proton conductivity of the polymers is in the range of 102 to 104.

In still another embodiment, the present invention provides the crystalline, two dimensional polymers of formula (I) wherein n represents number of benzimidazole units, where n is 3-6 but not 4.

The crystalline, two dimensional polymers of Formula (I) is selected from BIP-1, BIP-2 or BIP-3.

Imidazole covalently linked in the crystalline 2D-polymer backbone nullifies the stability and durability issues of the doping approach. The 2D-polymer structure exhibits ultra-high proton conductivity in the pristine form without any additional dopants such as imidazole, phosphoric acid. The crystalline, two dimensional polymers of Formula (I) are used in fuel cell, quasi-four-probe AC impedance measurements to find out the proton conductivity value.

In yet another embodiment, the present invention provides a process for the preparation of the crystalline, two dimensional polymers of Formula (I) comprising the steps of:
a) adding halogen to pyrene in a solvent at a temperature ranging from 25° C. to 30° C. to obtain a reaction mixture followed by stirring the reaction mixture at a temperature in the range of 100 to 150° C. for a time period in the range of 2 to 5 hours to obtain 1,3,6,8-tetrahalopyrene;
b) charging a mixture of boronic acid, 1,3,6,8-tetrahalopyrene of step (a), palladium catalyst, and a base in a solvent at a temperature in the range of 100 to 150°

C. for a time period in the range of 60 to 80 hours to obtain 1,3,6,8-tetrakis(4-(methoxycarbonyl)phenyl) pyrene;
c) heating a mixture of 1,3,6,8-tetrakis(4-(methoxycarbonyl)phenyl)pyrene of step (b) and a base in a solvent at a temperature in the range of 60 to 80° C. for a time period in the range of 8 to 10 hours followed by drying the solvent to obtain a residue;
d) adding water into the residue of step (c) followed by stirring at a temperature in the range of 25° C. to 30° C. for a time period in the range of 1 to 3 hours and adjusting pH in the range of 1 to 2 to obtain 1, 3, 6, 8-tetrakis (p-benzoic acid) pyrene; and
e) charging a mixture of 1,3,6,8-tetrakis(p-benzoic acid) pyrene of step (d), 1,2,4,5-benzenetetramine tetrahydrochloride and a catalyst in a solvent at a temperature in the range of 120° C. to 160° C. for a time period in the range of 45 to 48 hours to obtain a solution and continuing stirring at a temperature in the range of 180° C. to 200° C. for a time period in the range of 45 to 48 hours followed by adjusting pH of the solution to 8-9 to obtain the polymer;
wherein the polymer is a Benzimidazole-linked two dimensional polymer.

The halogen of step (a) is selected from bromine, chlorine or iodine.

The solvent of step (a) is selected from nitrobenzene, toluene or dimethyl formamide.

The boronic acid of step (b) is selected from 4-(methoxycarbonyl)phenyl)boronic acid or 4-Methoxycarbonylphenylboronic acid pinacol ester.

The palladium catalyst of step (b) is selected from tetrakis(triphenylphosphine) palladium or Palladium (II) acetate $(Pd(OAc)_2)$.

The solvent of step (b) is selected from dioxane, tetrahydrofuran or toluene.

The base of step (b) is selected from potassium tribasic phosphate, potassium carbonate, potassium acetate or sodium carbonate.

The base of step (c) is selected from sodium hydroxide (NaOH), potassium hydroxide or lithium hydroxide.

The solvent of step (c) is selected from tetrahydrofuran, dioxane, water or a mixture thereof, preferably the solvent is THF/water (ratio 1:1) mixture or dioxane:water (1:1).

The solvent of step (e) is selected from polyphosphoric acid; dioxane, tetrahydrofuran, toluene or a mixture thereof.

The catalyst of step (e) is polyphosphoric acid.

In a preferred embodiment, the present invention provides a process for the preparation of BIP-1 as shown in Scheme 1.

Scheme 1

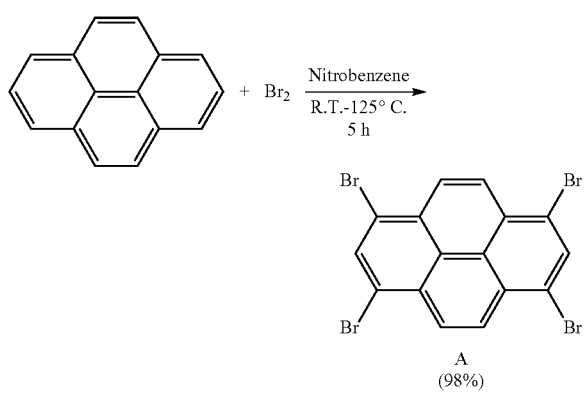

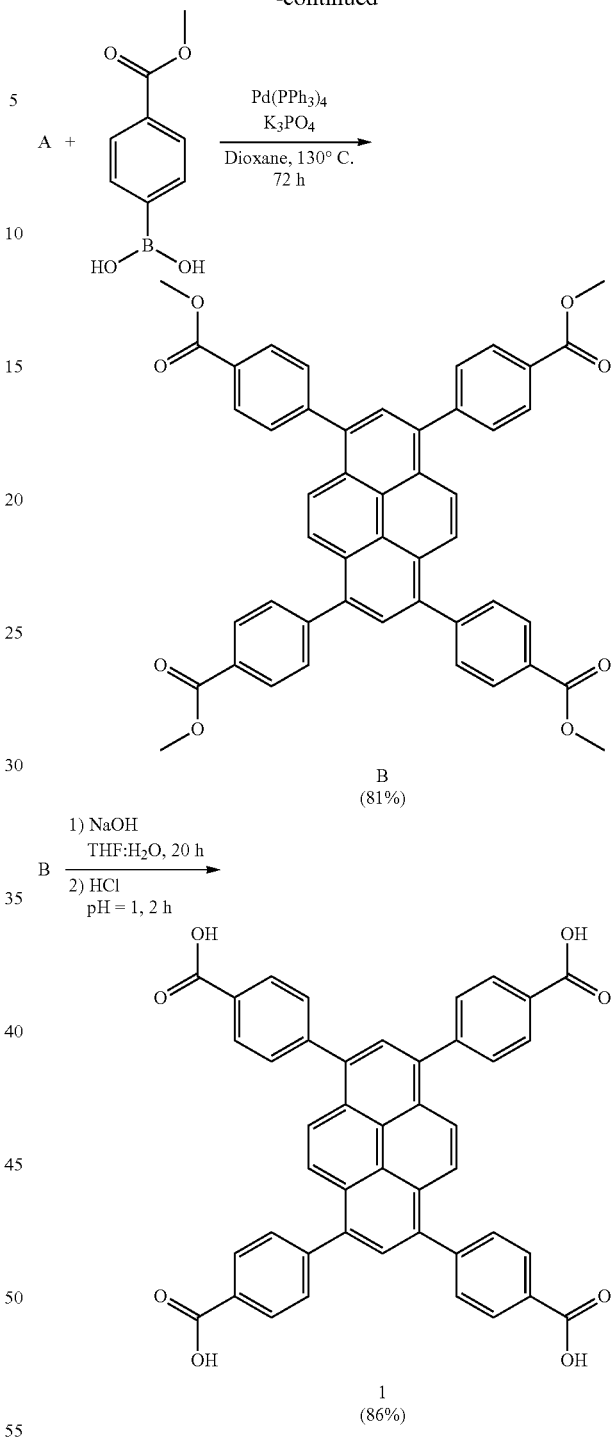

The present invention also provides a process for preparation of 1,4-bis (1H-benzo[d]imidazol-2-yl) benzene (3) comprising charging terephthalic acid, o-phenylenediamine, polyphosphoric acid (PPA) as solvent in presence of catalyst at 150° C. for 24 hours, further continuing stirring at the 190° C. for 24 hours under oxygen followed by adjusting the pH of the solution to 8-9 to obtain product of 1,4-bis (1H-benzo[d]imidazol-2-yl) benzene (3).

Scheme 2

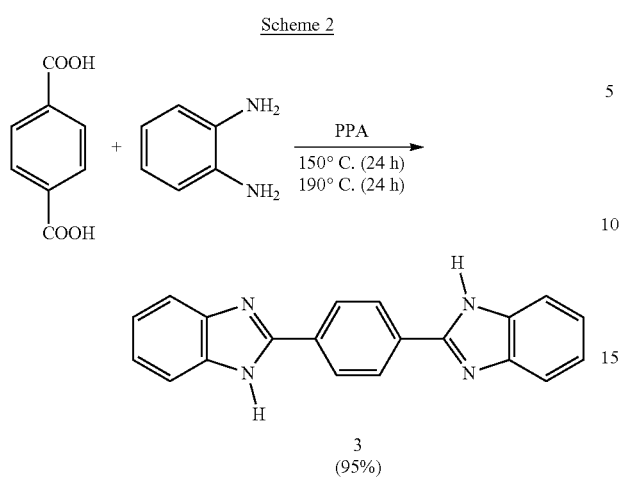

3
(95%)

The present invention also provides a process for preparation of model derivative 1, 3, 6, 8-tetrakis (4-(1H-benzo[d]imidazol-2-yl) phenyl) pyrene (pyrene imidazole model derivative) (4) comprising charging 1,3,6,8-tetrakis(p-benzoic acid) pyrene, o-phenylenediamine, polyphosphoric acid (PPA) as solvent in presence of catalyst at 150° C. for 24 hours further continuing stirring at the 190° C. for 24 hours under oxygen followed by adjusting the pH of the solution to 8-9 to obtain product of 1, 3, 6, 8-tetrakis (4-(1H-benzo[d]imidazol-2-yl) phenyl) pyrene (4).

Scheme 3

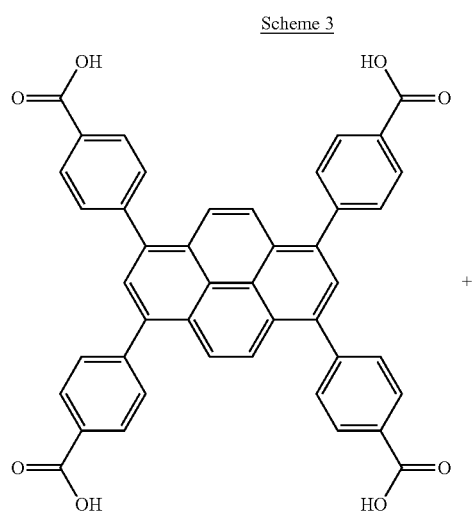

+

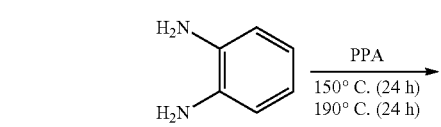

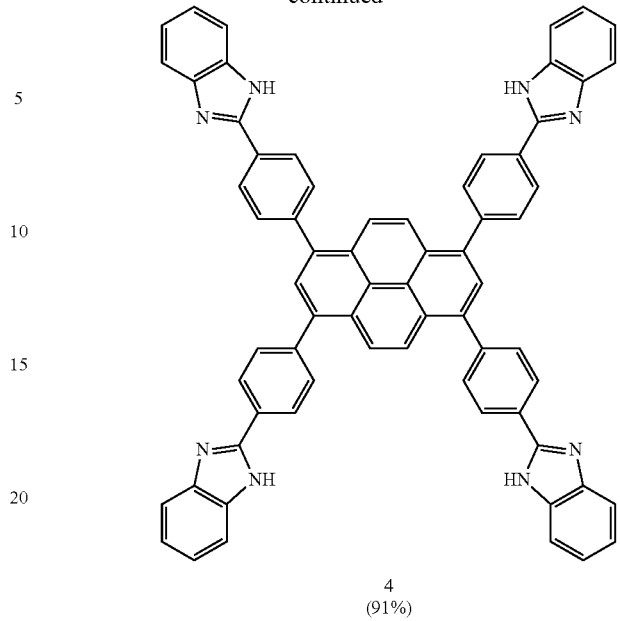

4
(91%)

FT-IR spectrum of BIP-1 reveals that the broad peak corresponds to N—H stretching in the range from 3412 cm$^{-1}$ (free N—H) to 3200 cm$^{-1}$ (hydrogen bonded N—H), while the intense new band that appeared at 1634 cm$^{-1}$ (C≡N) can be assigned to vibrations from the benzimidazole ring skeleton. The intensity of the C=O band at 1691 cm$^{-1}$ in (3) is substantially disappeared in BIP-1, suggesting the consumption of monomer during 2D-polymerization.

$^{13}$C cross-polarisation magic angle spinning ($^{13}$C CP-MAS NMR) spectrum of BIP-1 contains signals between 170 ppm-125 ppm arise from benzimidazole and other remaining aromatic units.

FIG. 1 depicts a) Photo of the reaction tube before polymerization with both monomers and PPA; b) Image of the reaction tube after polymerization after 48 hours; c) Photograph of polymer after isolation and d) picture of BIP-1 Pellet used for proton conductivity measurements.

Figure 2:
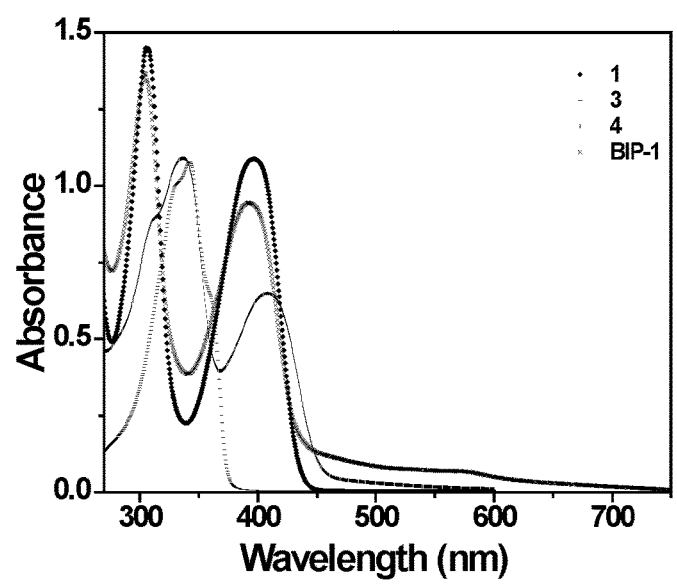
FIG. 2: Comparison of UV-Visible absorption spectra of 1, model derivatives 3, 4, and BIP-1 oligomers

FIG. 2 depicts a comparison of the UV-Vis absorption spectrum of BIP-1 oligomers with model derivatives that are absorbing in the 280-480 nm range, indicated the presence of benzimidazole moiety in the molecule. A broad peak exhibited by BIP-1 in solid state UV-Vis absorption similar to that of the model derivative 4, has also endorsed the polymerization.

Figure 3:
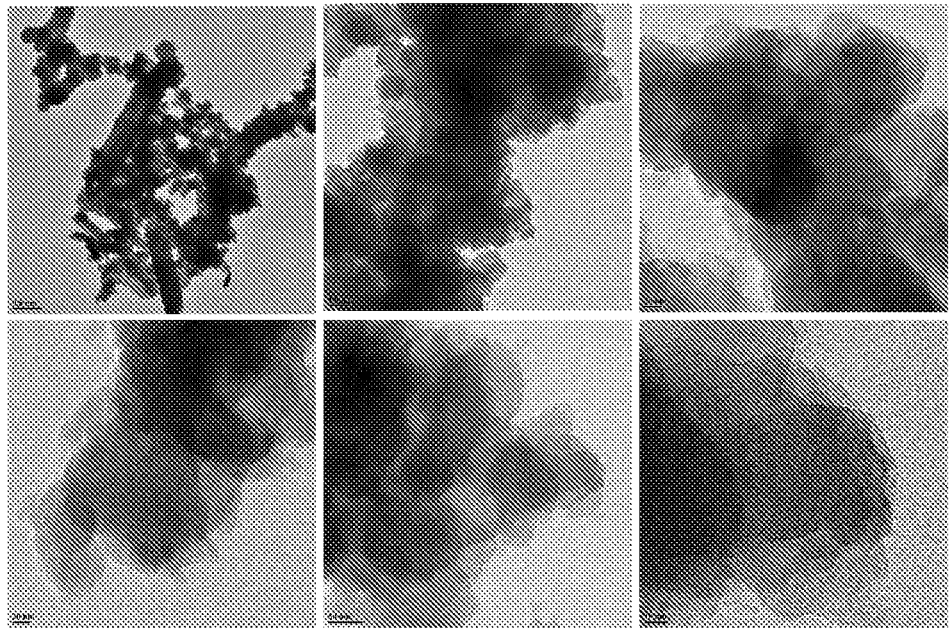
FIG. 3: TEM images of BIP-1 showing layered nature of 2D-sheets

FIG. 3 depicts that multilayer stacks of 2D-polymer structure as observed by transmission electron microscope (TEM) images of BIP-1 and points to both the extended 2D-polymerization and the preferable strong 7t-stacking between the layers. TEM images of BILP-1 (Imidazole linked Pyrene 2DP by acid route) samples were prepared by dispersing polymer in methanol 50 µl drop casted on the Cu grid.

Figure 4:
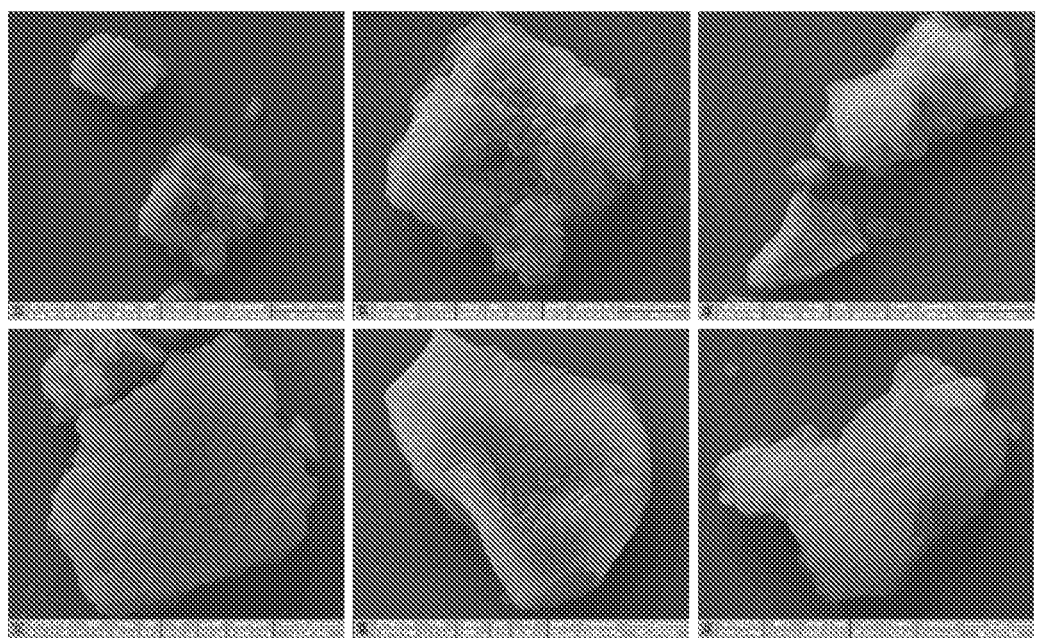
FIG. 4: SEM images of 2D-polymer showing the sheet morphology of the BIP-1, drop casted from MeOH suspension

FIG. 4 depicts that Scanning electron microscope (SEM) image of BIP-1 showed solid state feature of the 2D-polymer comprising of layered-sheets.

Figure 5:
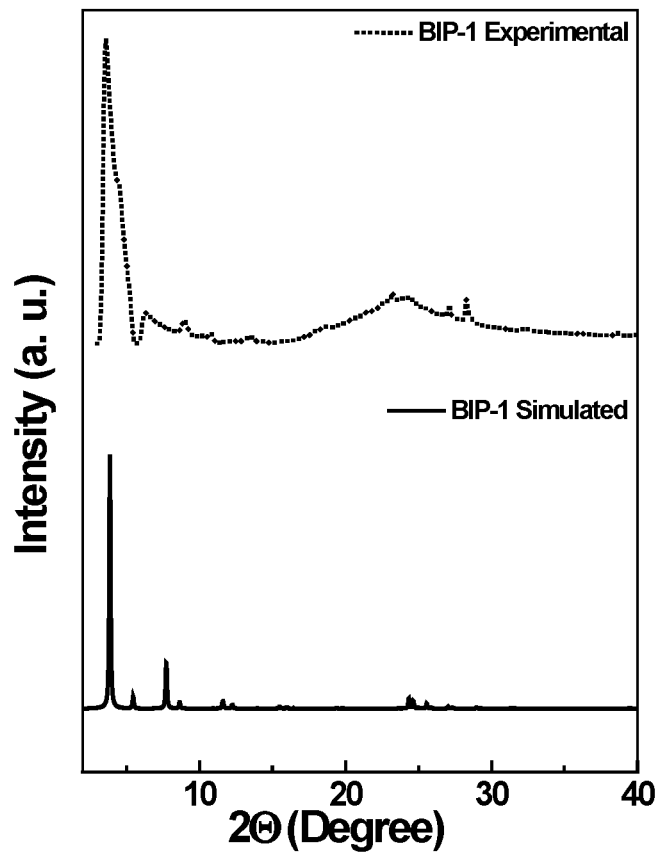
FIG. 5: Comparison of PXRD patterns of BIP-1 experimental (dotted) and simulated pattern for an AA stacking mode (solid)

FIG. 5 depicts comparison of PXRD patterns of BIP-1 experimental (dotted) and simulated pattern for an AA stacking mode (solid). Powder X-ray diffraction (PXRD) patterns of BIP-1 exhibited an intense peak at 3.7°, corresponding to the reflection from the (100) plane. The peak in the region 26=25° patterns of BIP-1 is due to the reflection from the (001) plane. The π-π stacking distance between 2D-polymer layers are calculated to be 3.3 and 3.6 Å from the d spacing between 001 plane. The AA stacking mode is confirmed by the peak position and intensity of the PXRD pattern.

Figure 6:
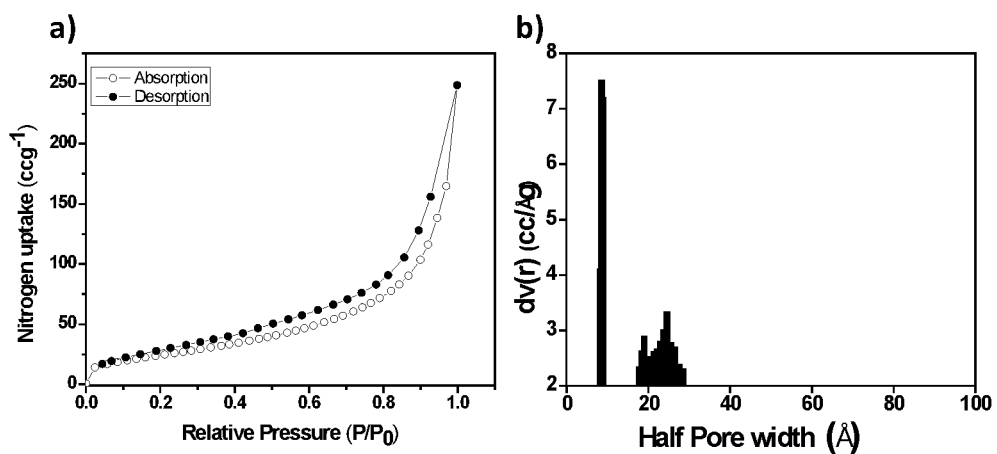
FIG. 6: a) BET $N_2$ sorption isotherm curves and b) pore-size distribution profile of BIP-1 measured at 77 K

FIG. 6 depicts a) BET $N_2$ sorption isotherm curves and b) pore-size distribution profile of BIP-1 measured at 77 K. Confirms the 2D-polymerization happened as shown in the scheme 2, resulting in well-defined porous polymer.

Figure 7:
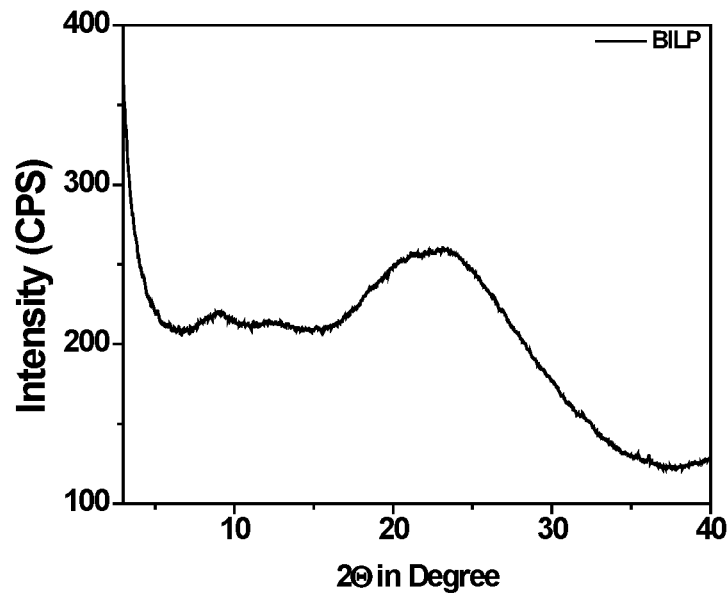
FIG. 7: PXRD pattern for BILP (H. M. El-Kaderi et al. J. Mater. Chem., 2012, 22, 25409-25417) sample reproduced, indicating amorphous materials.

FIG. 7 depicts PXRD-pattern for BILP (H. M. El-Kaderi group) sample reproduced, indicating amorphous materials. BILP-10 published by H. M. El-Kaderi et al.; the polymer has no long range ordering, evident from PXRD which lacks sharp peak in the PXRD. It is clear from the PXRD analysis of BIP-1 that new synthetic route helps to undergo thermodynamically controlled reversible condensation reaction of the monomers, which results in a crystalline framework.

Figure 8:
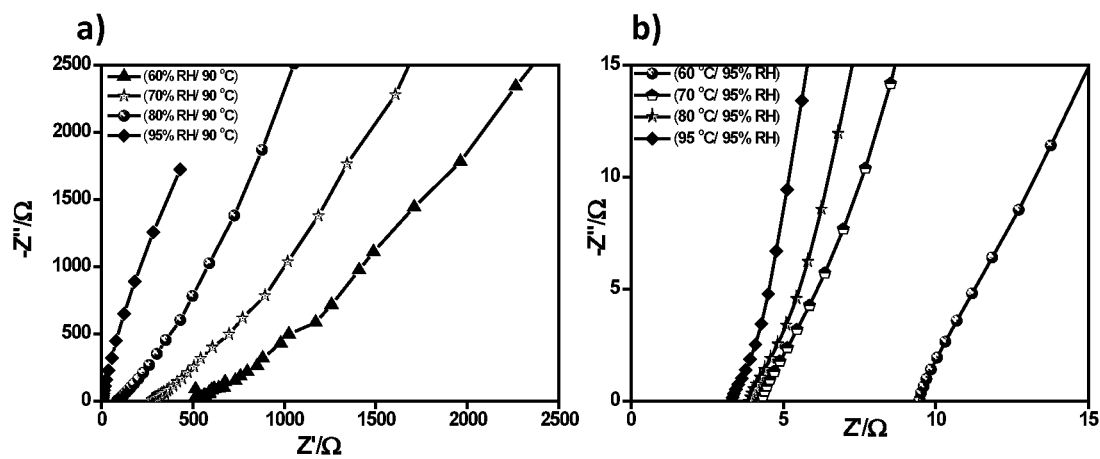
FIG. 8: Proton conductivity measurements carried out for BIP-1 (in compacted pellet of the powdered sample), using quasi-four-probe AC impedance measurements a) under different relative humidity at 95° C.; b) different temperature at 95% relative humidity humidified conditions in a homemade setup.

FIG. 8 depicts proton conductivity measurements carried out for BIP-1 (in compacted pellet of the powdered sample), using quasi-four-probe AC impedance measurements a) under different relative humidity at 95° C.; b) different temperature at 95% relative humidity humidified conditions in a home-made setup is placed between two stainless steel electrodes and the set up is placed inside a temperature controlled incubator which is also connected to a electrochemical work station. This experiment clearly shows that 95% relative humidity at 95° C., the material imparts least resistance and results the best proton conductivity of $3.2 \times 10^{-2}$ S $cm^{-1}$.

The benzimidazole linked pyrene 2D polymer (BILP-1) synthesized using aldehyde and amine, reported by El-Kaderi and co-workers also tested for proton conductivity and found that the values are pretty low in the order of $10^{-5}$ S $cm^{-1}$ only.

The polymer BIP-2 structure is predesigned to obtain a 2D polymer with increased imidazole linkages in periodic units with triangular pore structure. Hexakis(4-carboxyphenyl)benzene synthesized and characterized according to the report by Furukawa and coworkers (Inorg. Chem. 2015, 54, 10065-10072) as shown in the Scheme 4.

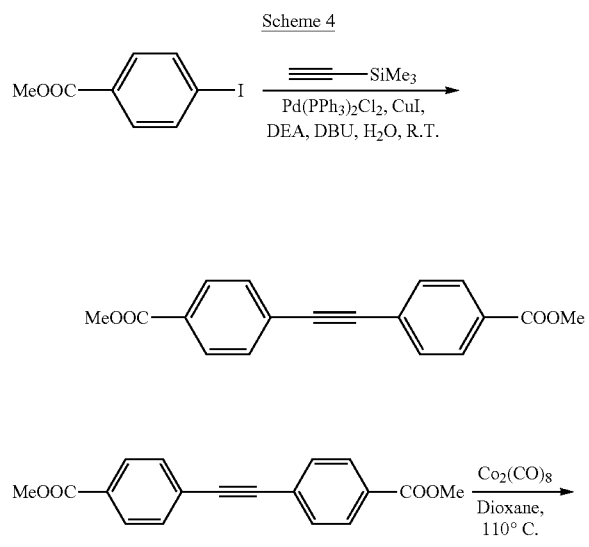

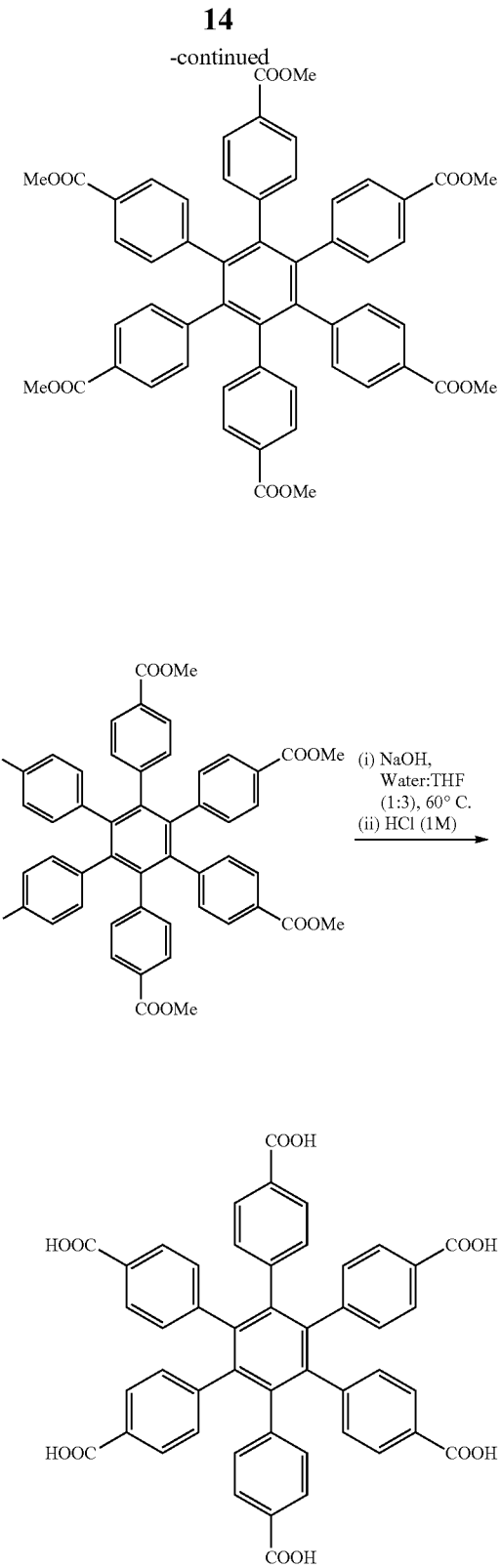

Synthetic scheme for the preparation of imidazole linked model derivative of BIP-2, 2,2'-(3',4',5',6'-tetrakis(4-(1H-benzo[d]imidazol-2-yl)phenyl)-[1,1':2',1''-terphenyl]-4,4''-diyl)bis(1H-benzo[d]imidazole) (6) is as shown in scheme 5.

Scheme 5

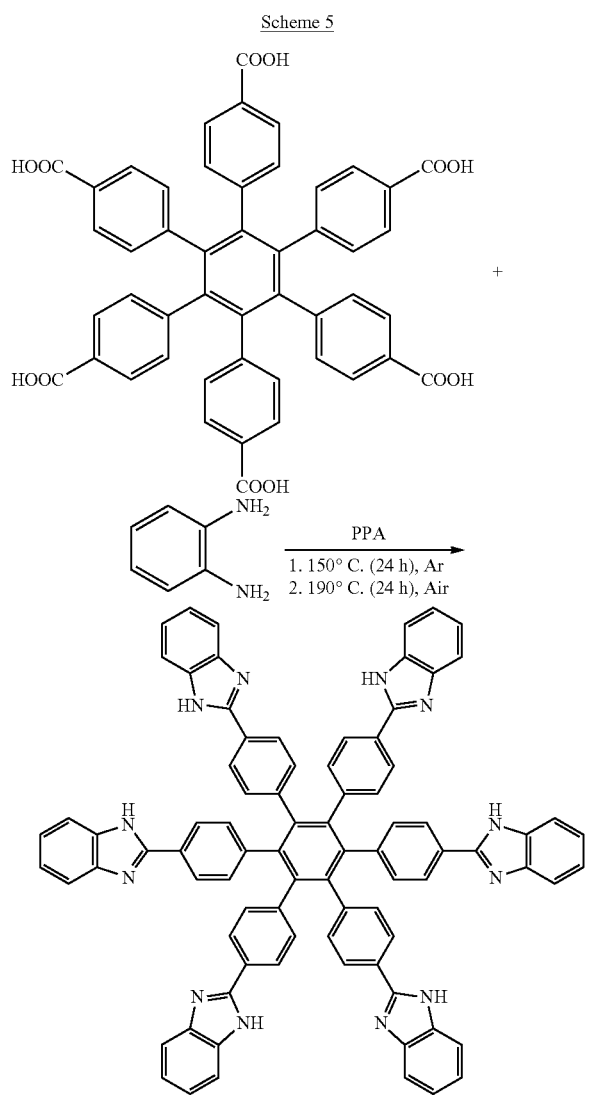

$^{13}$C CP-MAS NMR spectrum of BIP-2 observes a signal around 150 ppm that corresponds to NC(Ph)N in the benzimidazole units as well as other signals in the aromatic range, that arise from monomeric aromatic regions in the polymer repeating units.

Figure 9:
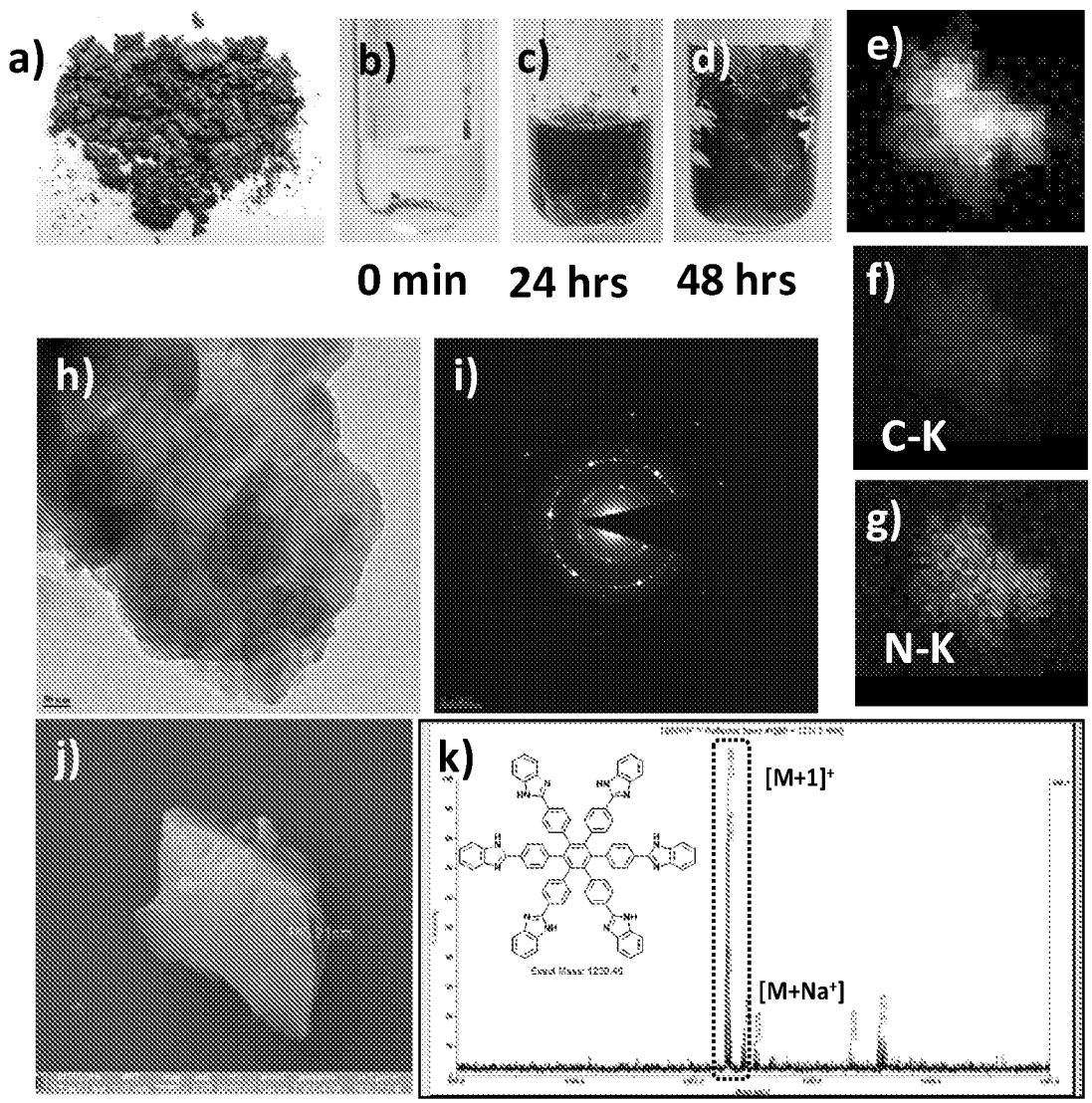
FIG. 9: a) Photograph of BIP-2 isolated solid, b-d) Photograph of BIP-2 polymerization image, e) high-angle annular dark-field (HAADF) image, TEM elemental mapping images of BIP-2 elemental mapping for f) C-K g) N-K h) TEM image of BIP-2 layered sheets i) Selected area diffraction measurements of BIP-2; j) SEM image of BIP-2 layered sheets; k) MALDI-TOF MS of model derivative of BIP-2 polymer.

FIG. 9 a denotes the photograph for the progress of polymerization and is monitored with time and after sufficient precipitation is observed, the reaction mixture is filtered and collected. The 2D-polymer is then kept overnight in saturated aqueous NaHCO$_3$ solution, again washed with water by soxhlet extraction until the filtrate is neutral to pH and followed in methanol for 12 hours in order to remove water from polymer matrix and is dried under vacuum. FIGS. 9(b) and 9(c) denotes that the multilayer stacks of 2D-polymer structure as revealed by TEM images of 2D-polymer suspension in methanol that points to both the extended 2D-polymerization and the preferable strong 7c-stacking between the layers. The extended polymerization is further confirmed by the scanning electron microscope (SEM) image.

FT-IR spectra of monomers 5, 2 and model derivative 6 and BIP-2 in KBr pellet observed broad bands from 3100 to 3235 cm$^{-1}$ corresponds to free N—H and hydrogen bonded N—H, new bands with stretching frequency at 1635 and 1360 cm$^{-1}$ corresponds to C=N and C—N, respectively. The absence of strong peak located at 1700 cm$^{-1}$ indicated the full consumption of both monomers containing carboxylic acid and amine functional moieties during the formation of benzimidazole unit.

Figure 10:
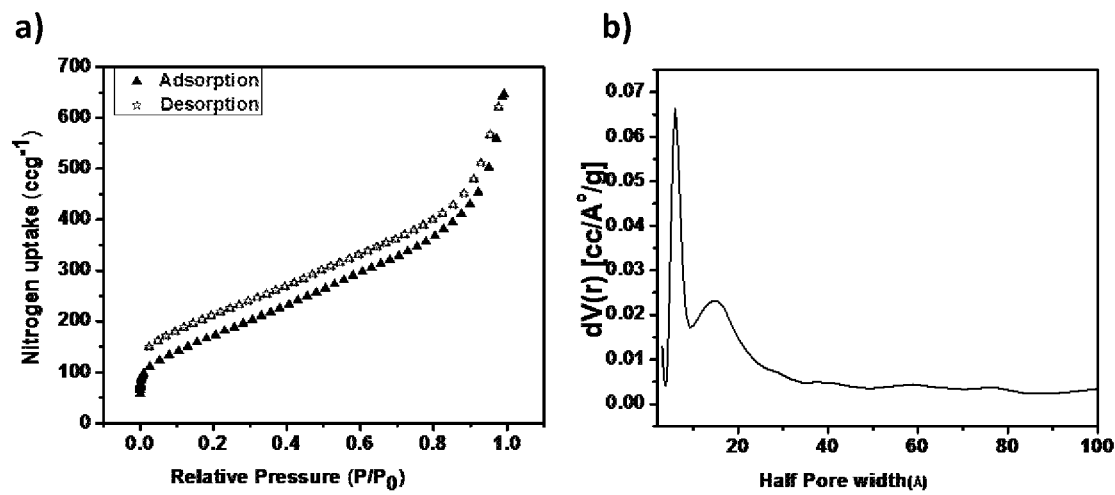
FIG. 10: a) BET $N_2$ sorption isotherm curves of BIP-2 measured at 77 K; b) Pore-size distribution profile of BIP-2

FIG. 10 denotes a) BET N$_2$ sorption isotherm curves of BIP-2 measured at 77 K; b) Pore-size distribution profile of BIP-2. Confirms the 2D-polymerization happened as shown in the scheme 7 resulting in well-defined porous polymer.

Figure 11:
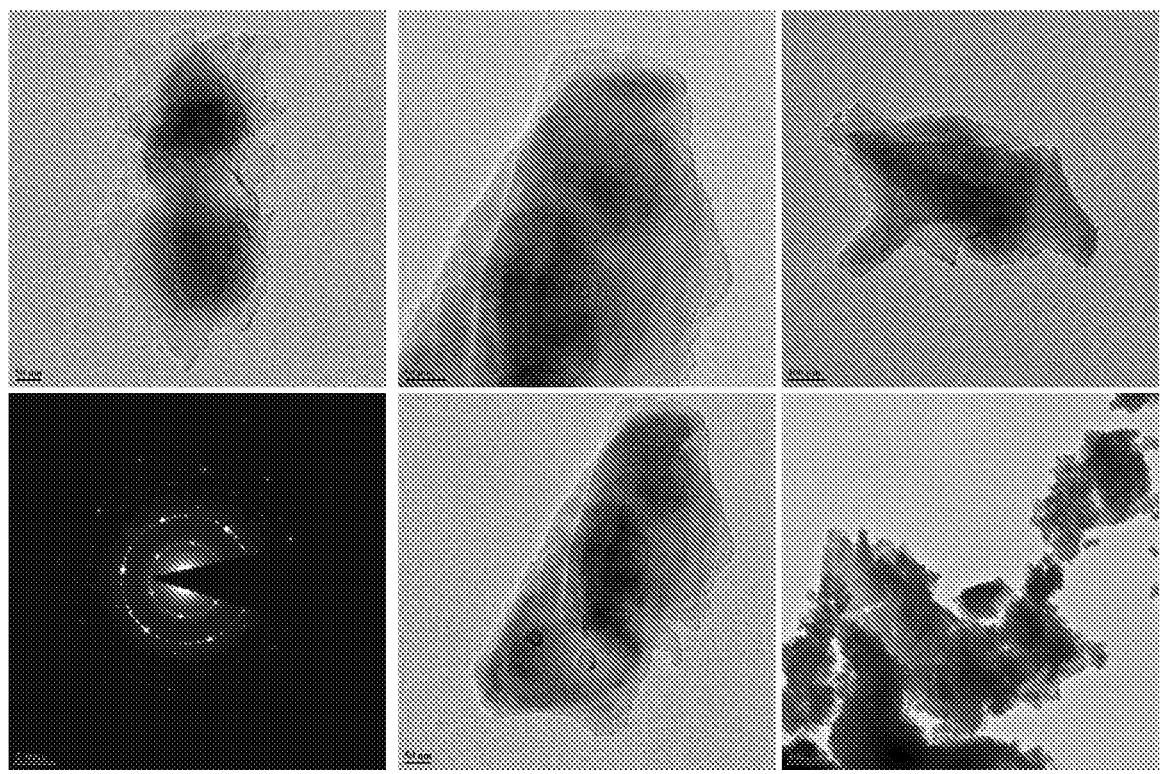
FIG. 11: TEM images of BIP-2

FIG. 11 depicts TEM images of BIP-2. TEM images of BIP-2 showing layered sheets, selected area diffraction (SAD) of BIP-2 showing crystalline ordering samples were prepared by dispersing polymer in methanol 20 µl drop casted on the Cu grid.

Figure 12:
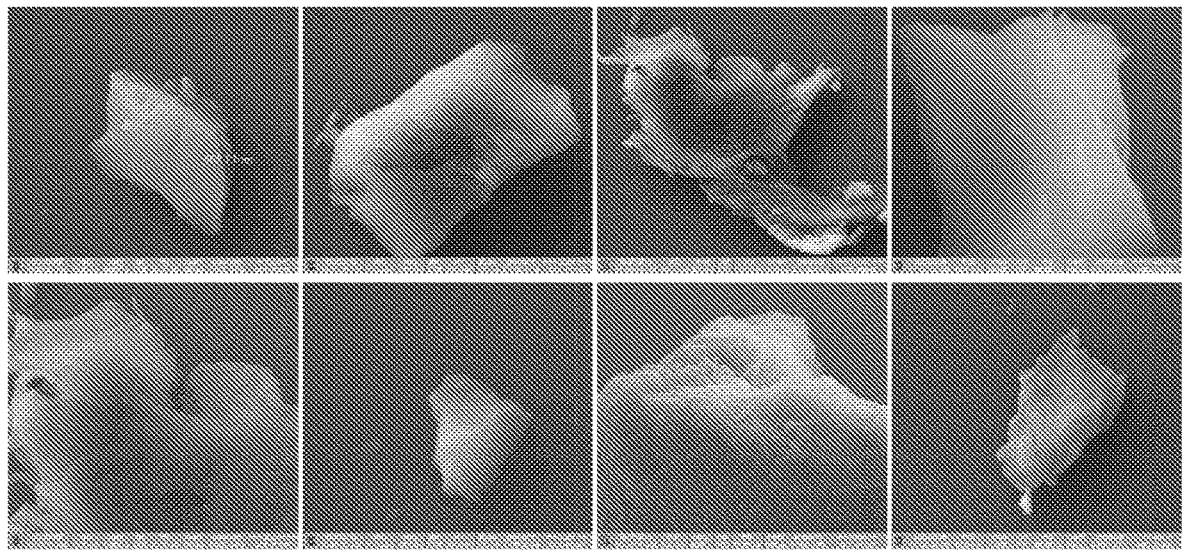
FIG. 12: SEM images of BIP-2

FIG. 12 depicts SEM images of BIP-2. SEM image of BIP-2 samples are prepared by dispersing polymer in methanol by sonication for about 5 min drop casted on silicon substrate, dried.

Figure 13:
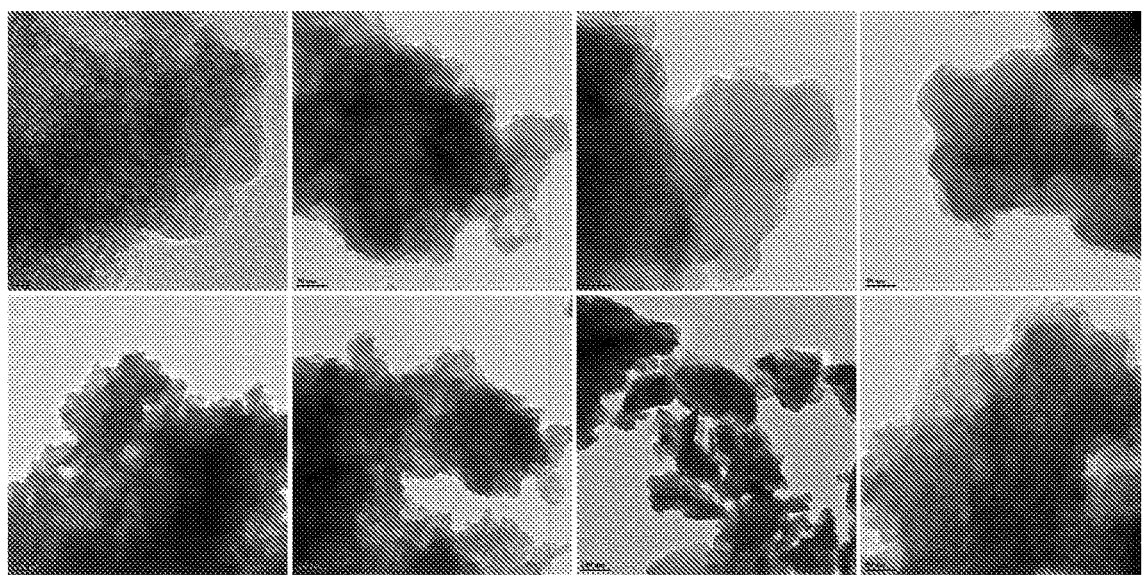
FIG. 13: TEM image of BIP-3

FIG. 13 depicts TEM images of BIP-3 showing layered sheets, samples are prepared by dispersing polymer in methanol 20 µl drop casted on the Cu grid.

Summary of quasi-four-probe AC impedance measurements under different temperature 95% relative humidified (RH) conditions BIP-1 (1.44 mm thick pellet)

TABLE 1

| | Temperature Variation at 95% RH | | |
| --- | --- | --- | --- |
| Sl. No | Condition | Resistance (Ohm) | Proton Conductivity (S/cm) |
| 1 | 60° C., 95% RH | 9.5 | $1.1 \times 10^{-2}$ |
| 2 | 70° C., 95% RH | 4.3 | $2.5 \times 10^{-2}$ |
| 3 | 80° C., 95% RH | 3.9 | $2.8 \times 10^{-2}$ |
| 4 | 95° C., 95% RH | 3.3 | $3.2 \times 10^{-2}$ |

Summary of quasi-four-probe AC impedance measurements under different humidified conditions at 95° C. BIP-1 (1.44 mm thick pellet)

TABLE 2

| | RH Variation at 95° C. | | |
| --- | --- | --- | --- |
| Sl. No | Condition | Resistance (Ohm) | Proton Conductivity (S/cm) |
| 1 | 95° C., 60% RH | 540 | $2.0 \times 10^{-4}$ |
| 2 | 95° C., 70% RH | 275 | $3.9 \times 10^{-4}$ |
| 3 | 95° C., 80% RH | 86 | $1.2 \times 10^{-3}$ |
| 4 | 95° C., 95% RH | 3.3 | $3.2 \times 10^{-2}$ |

Figure 14:
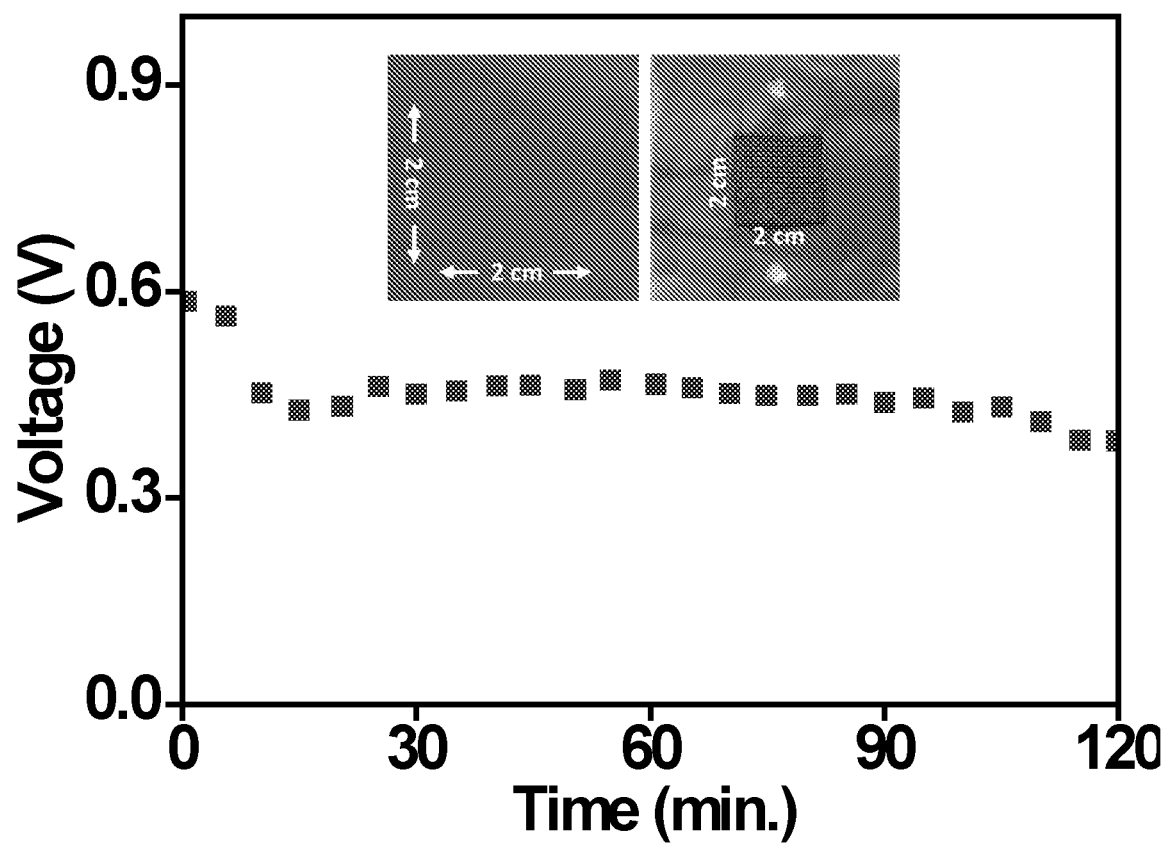
FIG. 14: The fuel cell life test of the BIP-1 membrane is performed at open-circuit voltage condition

FIG. 14 depicts the fuel cell life test of the BIP-1 membrane at open-circuit voltage condition. Insets show the photographs of BIP-PMMA membrane (4 cm$^2$) (left) and MEA by sandwiching BIP-PMMA membrane between two electrodes, maintaining an active area of 4 cm$^2$ (right). The open-circuit voltage remains stable for more than 1 h after an initial dip.

EXAMPLES

Following examples are given by way of illustration therefore should not be construed to limit the scope of the invention.

Example 1: Synthesis of 1, 3, 6, 8-tetrabromopyrene

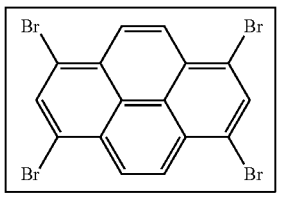 [SMILES: Brc1cc(Br)c2ccc3c(Br)cc(Br)c4ccc1c2c43]

To pyrene 1.01 g (5.0 mmol) in nitrobenzene (15 mL) was added bromine 3.52 g (22.0 mmol) dropwise at room temperature, and the mixture was stirred at 120° C. for 4 h. The reaction mixture was filtered, and the residue was washed with methanol (50 mL) and acetone (50 mL). After drying under reduced pressure, 1,3,6,8-tetrabromopyrene was obtained as a pale yellow solid in 2.54 g, Yield: 98%. (due to poor solubility, 1,3,6,8-tetrabromopyrene is not characterized in this step and directly used for the next step)

Example 2: Synthesis of 1, 3, 6, 8-tetrakis (4-(methoxycarbonyl)phenyl)pyrene

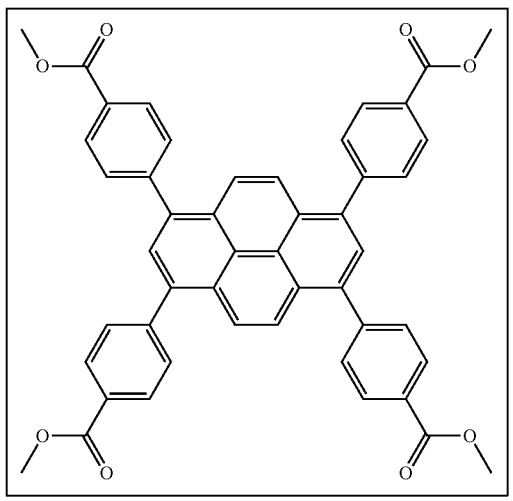

A mixture of 4-(methoxycarbonyl)phenyl)boronic acid 1.040 g (5.80 mmol), 1,3,6,8-tetrabromopyrene 0.500 g (0.97 mmol), tetrakis(triphenylphosphine) palladium (0) 0.030 g (0.026 mmol), and potassium tribasic phosphate 1.1 g (5.30 mmol) in dry dioxane (20 mL) was charged in a 30 mL sealed tube filled with argon and capped. This mixture was stirred under argon for 72 h at 130° C. in an oil bath. The reaction mixture was evaporated to dryness and the solid residue was washed with water to remove inorganic salts. The insoluble material was extracted with chloroform (three times by 50 mL), and the solvent volume was reduced under vacuum. The residue was boiled in tetrahydrofuran for two hour and filtered; the resulting filtrate contained mainly impurities. Pure 1,3,6,8-tetrakis(4-(methoxycarbonyl)phenyl)pyrene obtained as an yellow solid, 0.58 g, Yield: 82%.[2]

$^1$H NMR (400 MHz, CDCl$_3$): δ ppm 4 (s, 12H), 7.76 (d, 8H), 8.02 (s, 2H), 8.16 (s, 4H), 8.24 (d, 8H). MALDI-TOF MS: m/z calculated for C$_{48}$H$_{34}$O$_8$[M]$^+$: 738.2254, found: 738.1611.

FT-IR (KBr): 2954, 1724, 1606, 1428, 1275, 1107, 710 cm$^{-1}$.

Example 3: 1, 3, 6, 8-tetrakis (p-benzoic acid) pyrene (1)

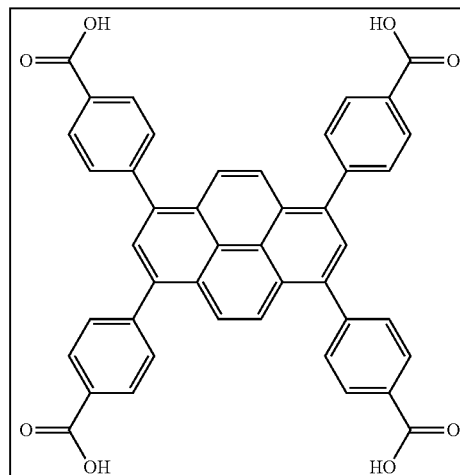

To a 250 mL round bottom flask containing 0.58 g (0.78 mmol) of solid 1,3,6,8-tetrakis(4-(methoxycarbonyl)phenyl) pyrene, a solution containing 1.5 g (37.5 mmol) NaOH in 100 mL of a THF/water (ratio 1:1) mixture was added and the resultant suspension was vigorously stirred under reflux overnight. The solvents were removed under vacuum and water was added to the residue which formed a clear yellow solution. The clear yellow solution was stirred at room temperature for 2 h and the pH value was adjusted to 1 using concentrated HCl. The resulting yellow solid was collected by filtration, and washed with water several times. The crude product was recrystallized from DMF, filtered, washed with chloroform and dried under vacuum. This gave the pure product, as yellow solid 0.49 g, Yield: 91%.

$^1$H NMR (400 MHz, DMSO-d$_6$): δ ppm 7.82 (d, 8H), 8.05 (s, 2H), 8.12 (d, 8H), 8.17 (s, 4H), 13.11 (s, 4H). MALDI-TOF MS: m/z calculated for C$_{44}$H$_{26}$O$_8$[M]$^+$: 682.1628, found: 682.1432. FT-IR (KBr): 3414-3070, 2893, 1691, 1610, 1423, 1285, 859 cm$^{-1}$.

Example 4: Benzimidazole-linked 2D-polymer (BIP-1)

Teflon capped pressure tube (10 ml) filled with argon was charged with 20 mg (30 μmol) 1,3,6,8-tetrakis(p-benzoic acid) pyrene, 17 mg (60 μmol) of 1,2,4,5-benzenetetramine tetrahydrochloride (2) and in the presence of 3 mL of PPA as solvent and catalyst. The reaction was stirred at 150° C. for 48 h and then stirred at 190° C. for 48 h under oxygen. After the pH of the resulting mixture was adjusted to 8-9 with saturated NaHCO$_3$, 2D-polymer was precipitated. After filtration, the polymer was obtained as dark coloured powder. The powder collected and then soxhlet extraction was performed with water, methanol, acetone for 12 hours and then dried at 100° C. under vacuum for 12 hours to give a dark coloured powder, 32 mg, Yield (Isolated): 80%.

Scheme 6

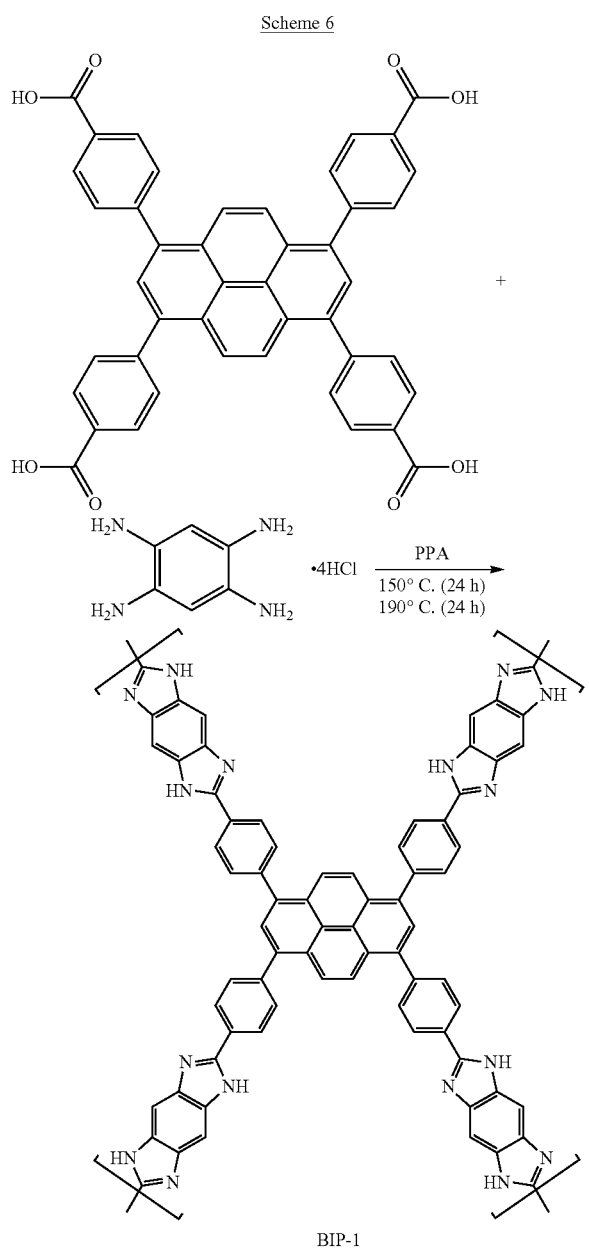

BIP-1

Example 5: Model derivative 1: 1,4-bis(1H-benzo[d]imidazol-2-yl) benzene (3)

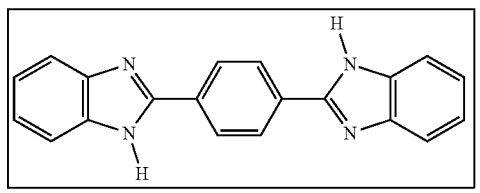 [SMILES: c1ccc2[nH]c(-c3ccc(-c4nc5ccccc5[nH]4)cc3)nc2c1]

Teflon capped pressure tube (10 ml) filled with argon, was charged with 20 mg (120 μmol) of terephthalic acid, 26 mg (240 μmol) of o-phenylenediamine in the presence of 3 mL of polyphosphoric acid (PPA) as solvent, catalyst. The reaction was heated at 150° C. for 24 h and then stirred at 190° C. for 24 h under oxygen. After the pH of the resulting mixture was adjusted to 8-9 with saturated sodium hydrogen carbonate ($NaHCO_3$), product was precipitated. Thus obtained crude product was then further purified by recrystallization with methanol to give pure 1, 4-bis (1H-benzo[d]imidazol-2-yl) benzene, as a pale off white solid, 34 mg, Yield: 91%.[3]

$^1$H NMR (500 MHz, DMSO-$d_6$): δ ppm 7.26 (m, 4H), 7.69 (m, 4H), 8.35 (s, 4H), 13.13 (s, 2H). MALDI-TOF MS: m/z calculated for $C_{20}H_{14}N_4$ [M]$^+$: 310.1218, found: 310.979.

FT-IR (KBr): 3420, 3046, 2917, 1643, 1438, 1318, 1117, 734.

Example 6: Model derivative 2: 1, 3, 6, 8-tetrakis (4-(1H-benzo[d]imidazol-2-yl) phenyl) pyrene (pyrene imidazole model derivative) (4)

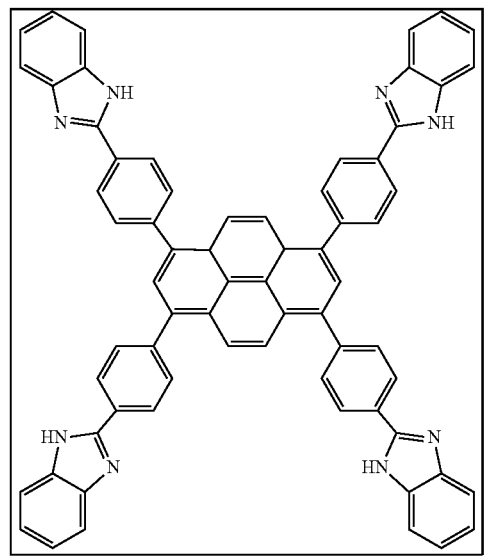 [SMILES: C1=CC2C(c3ccc(-c4nc5ccccc5[nH]4)cc3)=CC(c3ccc(-c4nc5ccccc5[nH]4)cc3)=c3ccc4c(c32)C1C(c1ccc(-c2nc3ccccc3[nH]2)cc1)=CC=4c1ccc(-c2nc3ccccc3[nH]2)cc1]

Teflon capped pressure tube (10 ml) filled with argon, was charged with 20 mg (30 μmol) of 1,3,6,8-tetrakis(p-benzoic acid) pyrene, 14.2 mg of o-phenylenediamine (131 μmol) in the presence of 3 mL of PPA as solvent, catalyst. The reaction was heated at 150° C. for 24 h and then stirred at 190° C. for 24 h under oxygen. After the pH of the resulting mixture was adjusted to 8-9 with saturated sodium hydrogen carbonate ($NaHCO_3$), product was precipitated. Thus obtained crude product was then further purified by recrystallization with methanol to give pyrene imidazole model derivative, as a pale yellow solid, 24 mg, Yield: 84%.

$^1$H NMR (500 MHz, DMSO-$d_6$): δ ppm 7.27 (m, 8H), 7.6 (d, 4H), 7.73 (d, 4H), 7.98 (d, 8H), 8.22 (m, 4H), 8.37 (s, 4H), 8.45 (d, 8H), 13.11 (s, 4H). MALDI-TOF MS: m/z calculated for $C_{68}H_{42}N_8$[M]$^+$: 970.3532, found: 970.0503.

FT-IR (KBr): 3390, 3261, 1648, 1209, 1146, 897, 701.

Example 7: The synthesis of 2,2'-(3',4',5',6'-tetrakis (4-(1H-benzo[d]imidazol-2-yl)phenyl)-[1,1':2',1''-terphenyl]-4,4''-diyl)bis(1H-benzo[d]imidazole) (6)

Teflon capped pressure tube (10 ml) filled with argon, was charged with 25 mg (31.3 gmol) of Hexakis(4-carboxyphenyl)benzene, 20.6 mg of o-phenylenediamine (190.9 μmol) in the presence of 3 mL of PPA as solvent, catalyst. The reaction was heated at 150° C. for 24 h and then stirred at 190° C. for 24 h under oxygen. After the pH of the resulting mixture was adjusted to 8-9 with saturated sodium hydrogen carbonate (NaHCO$_3$), product was precipitated. Thus obtained crude product was then further purified by recrystallization with methanol to give 2,2'-(3',4',5',6'-tetrakis(4-(1H-benzo[d]imidazol-2-yl)phenyl)-[1,1':2',1''-terphenyl]-4,4''-diyl)bis(1H-benzo[d]imidazole), as a pale yellow solid, 31 mg, Yield: 80%.

MALDI-TOF MS: m/z calculated for $C_{68}H_{43}N_8[M+1]^+$: 1231.47, found: 1231.2944. $C_{84}H_{55}N_{12}Na^+$ $[M+1+Na]^+$: 1254.45 found: 1254.2770. FT-IR (KBr): 3100-3400, 1635, 1395, 1123, 850, 742.

Example 8: Synthesis of BIP-2

Teflon capped pressure tube (10 ml) filled with argon was charged with 25 mg (31.3 μmol) hexakis(4-carboxyphenyl) benzene, 26.67 mg (93.9 μmol) of 1,2,4,5-benzenetetramine tetrahydrochloride and in the presence of 3 mL of PPA as solvent and catalyst. The reaction was stirred at 150° C. for 48 h and then stirred at 190° C. for 48 h under oxygen. After the pH of the resulting mixture was adjusted to 8-9 with saturated sodium NaHCO$_3$, 2D-polymer was precipitated. After filtration, the polymer was obtained as dark colored powder. The powder was collected and then soxhlet extraction was performed with water, methanol, acetone for 12 hours and then dried at 100° C. under vacuum for 12 hours to give a dark colored powder, 36 mg. Yield (Isolated): 76%.

Scheme 7

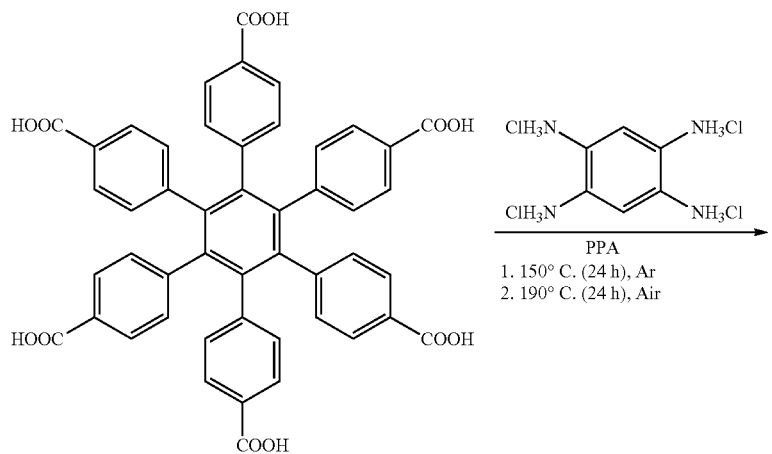

Example 9: The preparation of 1,3,5-tris(1H-benzo[d]imidazol-2-yl)benzene model derivative A Teflon capped pressure tube (10 ml) filled with argon, was charged with 25 mg (118.9 μmol) of benzene-1,3,5-tricarboxylic acid, 38.6 mg of o-phenylenediamine (356.9 μmol) in the presence of 3 mL of PPA as solvent, catalyst. The reaction was heated at 150° C. for 24 h and then stirred at 190° C. for 24 h under oxygen. After the pH of the resulting mixture was adjusted to 8-9 with saturated $NaHCO_3$, product was precipitated. Thus obtained crude product was then further purified by reprecipitation with methanol to give 1,3,5-tris(1H-benzo[d]imidazol-2-yl)benzene, as a pale yellow solid, 40 mg, Yield: 78%. MALDI-TOF MS: m/z calculated for $C_{27}H_{18}N_6[M+1]^+$: 427.16, found: 427.065.

Scheme 8

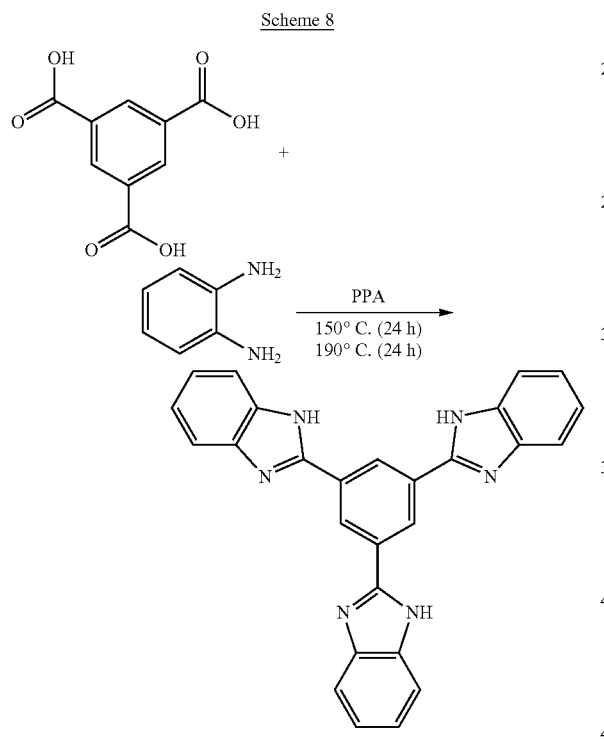

Example 10: Procedure for the synthesis for benzimidazole 2D-polymer BIP-3

Teflon capped pressure tube (10 ml) filled with argon was charged with 40.5 mg (142.7 μmol) benzene-1,3,5-tricarboxylic acid, 20 mg (95.1 μmol) of 1,2,4,5-benzenetetramine tetrahydrochloride and in the presence of 3 mL of PPA as solvent and catalyst. The reaction was stirred at 150° C. for 48 h and then stirred at 190° C. for 48 h under oxygen. After the pH of the resulting mixture was adjusted to 8-9 with saturated sodium hydrogen carbonate ($NaHCO_3$), 2D-polymer was precipitated.

Scheme 9

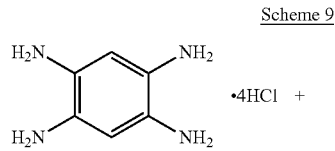

·4HCl +

-continued

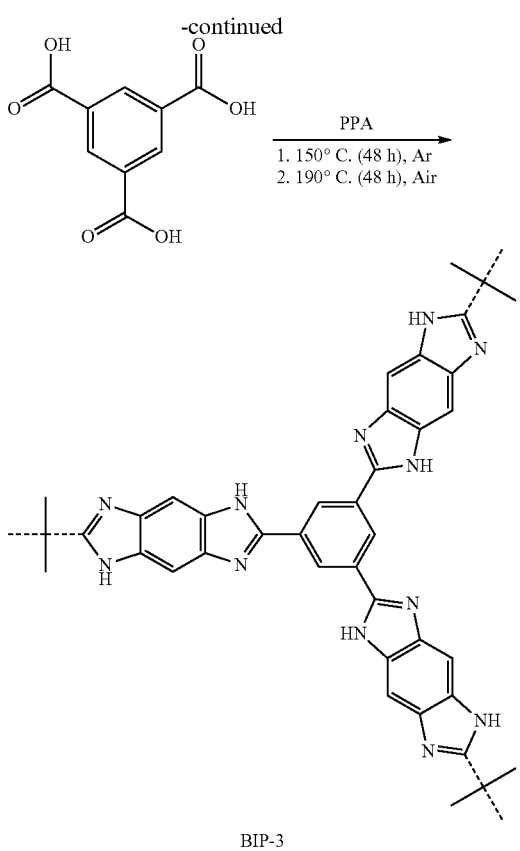

BIP-3

Example 11: Experimental Procedure for Proton Conductivity

Proton conducting ability was investigated using two-probe A.C impedance measurements under humidified conditions. In a home-made setup, pellet(13 mm diameter) was placed between two stainless steel electrodes and the set up was placed inside a temperature controlled humidity chamber (SH-241, ESPEC Co. Ltd., Japan), which was also connected to a BioLogic electrochemical work station (VMP-3). The sample was left to equilibrate at each temperature for at least 1 h or until a steady state was reached. The electrochemical impedance measurements were performed in the frequency range of 1 MHz-0.1 Hz using input voltage amplitude of 10 mV.

Example 12: Conductivity Measurement

Total of 190 mg of BIP sample was pressed into a die under 1000 psi for 2 min curing time to obtain uniform pellets (~1.2 mm in thickness, 13 mm in diameter). In case of BIP pellet the proton conductivity is measured at different temperatures (from 60° C. to 95° C.) under 95% RH. In each case, the proton conductivity is calculated using the Pouillet's equation, $\sigma=L/(R \times A)$, wherein σ is the conductivity ($Scm^{-1}$), L is the thickness of the measured sample (cm) and A is the electrode area ($incm^2$). The resistance is calculated using the high frequency intercept of the Nyquist plot measured by the impedance spectroscopy.

Example 13: Preparation of BIP Membrane

BIP membrane was prepared by a film casting method using a BIP (35 wt %)-PMMA mixture in dimethylacetamide (DMAc). A slurry of BIP and Polymethyl methacrylate (PMMA) in DMAc was prepared by sonication and followed by stirring at 80° C. for 12 h. The membrane was casted by pouring the slurry onto a Petri dish; majority of the solvent was evaporated in a ventilated oven at a temperature of 80° C. after 3 hours. The membrane was then peeled off, washed with water to remove the residual DMAc, and dried in an oven at 110° C. for 12 h.

Example 14: The Fuel Cell Experiments

The Fuel cell experiments were performed in a Fuel Cell Technologies Inc., instrument. The operation temperature was 50° C. and at 100% RH. The gas feeding conditions were $H_2$ (100 sccm) and $O_2$ (100 sccm) respectively. The membrane electrode assembly (MEA) was made by sandwiching the electrodes with the membrane. For this, Pt/C (40 wt %) was brush coated on a gas diffusion layer with a Platinum loading of 1 mg $cm^{-2}$. The anode and cathode electrodes were having an active area of 4 $cm^2$ and the membrane is kept in between the electrodes. The assembly was hot pressed at 0.5 ton for 1 minute at 130° C. and obtained the MEA. In a fuel cell fixture, MEA was fixed between the graphite plates and the life test was performed at the open circuit voltage (OCV) conditions.

Advantages of the Invention

1. Enhancement of conductivity and enables ultrahigh proton-conduction in pristine form without any additional dopants.
2. Crystalline material was obtained starting with an acid (in place of an aldehyde) and good yields were obtained indicating the cyclization was completed
3. Provides framework tunability
4. Chemically stable
5. Easy material fabrication
6. Feasibility of hybridization with other materials
7. Sustainable in harsh fuel cell operating conditions
8. Large surface area and lightweight

We claim:
1. A crystalline, two dimensional polymer of Formula (I),

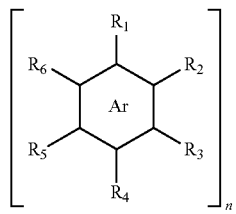

Formula (I)

wherein $R_1$ to $R_6$ are selected from hydrogen and

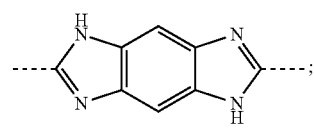

wherein n is the number of repeating units of $R_1$ to $R_6$ and n is in the range of 3 to 6 but not 4; and
wherein Ar is an aromatic ring;

provided that, from $R_1$ to $R_6$ at least one is

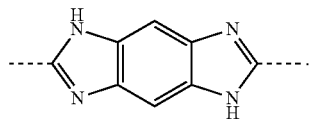

2. The polymer of formula (I) as claimed in claim 1, wherein said $R_1$ to $R_6$ are selected from hydrogen and

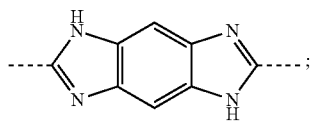

and
wherein Ar is selected from

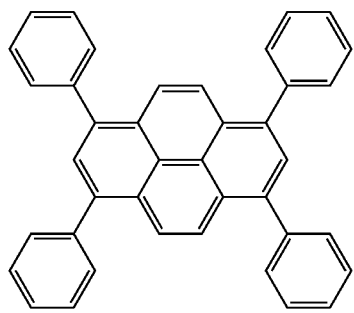

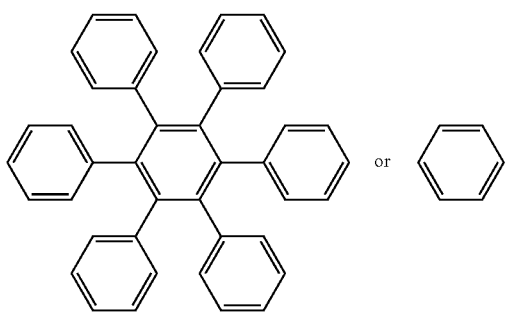

provided that at least one $R_1$ to $R_6$ is

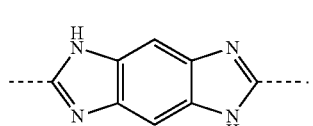

3. The polymer of formula (I The polymer of formula (I) as claimed in claim 1, wherein said polymer is selected from BIP-1, BIP-2 or BIP-3; having formula as:

BIP-1
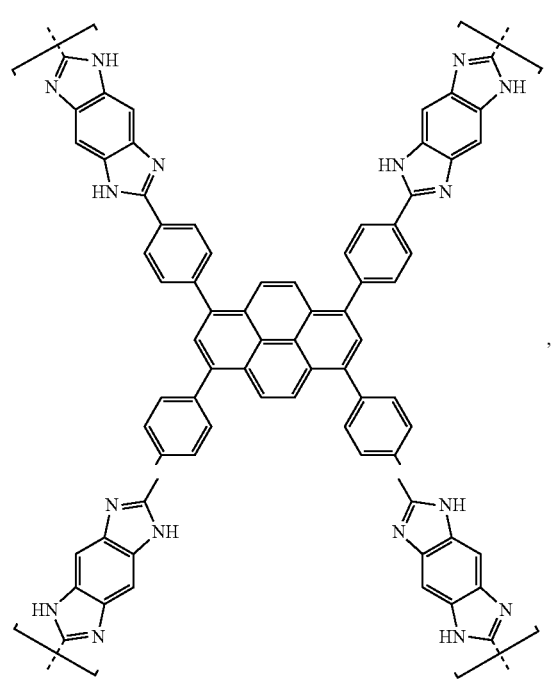
BIP-2
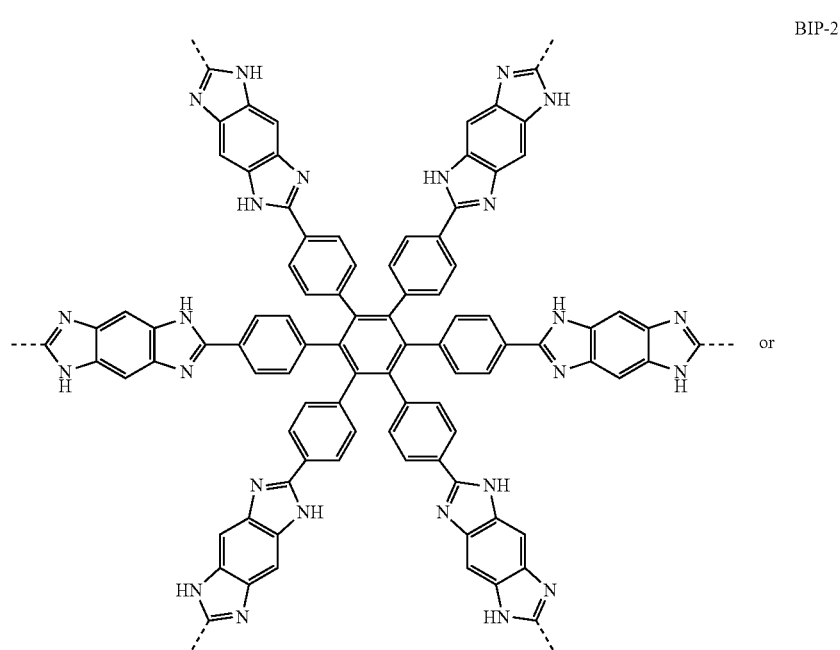 or

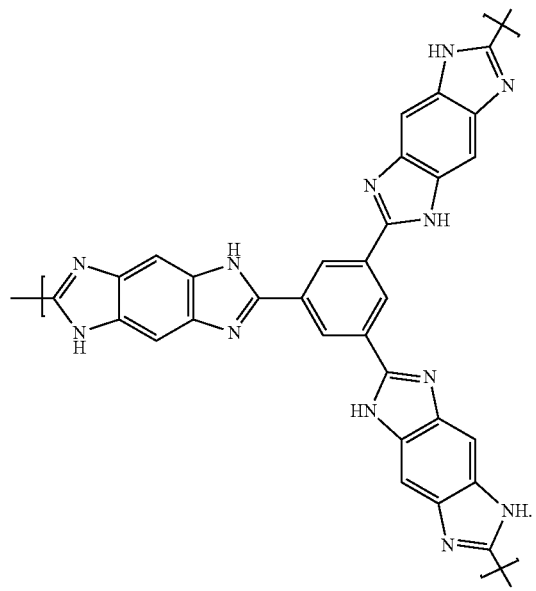

BIP-3

4. A process for preparation of the crystalline, two dimensional polymers of Formula (I) as claimed in claim 1 comprising:
  a) adding halogen to pyrene in a solvent at a temperature ranging from 25° C. to 30° C. to obtain a reaction mixture followed by stirring the reaction mixture at a temperature in the range of 100 to 150° C. for a time period in the range of 2 to 5 hours to obtain 1,3,6,8-tetrahalopyrene;
  b) charging a mixture of boronic acid, 1,3,6,8-tetrahalopyrene of step (a), palladium catalyst and a base in a solvent at a temperature in the range of 100 to 150° C. for a time period in the range of 60 to 80 hours to obtain 1,3,6,8-tetrakis(4-(methoxycarbonyl)phenyl)pyrene;
  c) heating a mixture of 1,3,6,8-tetrakis(4-(methoxycarbonyl)phenyl)pyrene of step (b) and a base in a solvent at a temperature in the range of 60 to 80° C. for a time period in the range of 8 to 10 hours followed by drying the solvent to obtain a residue;
  d) adding water into the residue of step (c) followed by stirring at a temperature in the range of 25° C. to 30° C. for a time period in the range of 1 to 3 hours and adjusting pH in the range of 1 to 2 to obtain 1, 3, 6, 8-tetrakis (p-benzoic acid) pyrene; and
  e) charging a mixture of 1,3,6,8-tetrakis(p-benzoic acid) pyrene of step (d), 1,2,4,5-benzenetetramine tetrahydrochloride and a catalyst in a solvent at a temperature in the range of 120° C. to 160° C. for a time period in the range of 45 to 48 hours to obtain a solution and continuing stirring at a temperature in the range of 180° C. to 200° C. for a time period in the range of 45 to 48 hours followed by adjusting pH of the solution to 8-9 to obtain the polymer;

wherein the polymer is a Benzodiimidazole-linked two dimensional polymer.

5. The process as claimed in claim 4, wherein said halogen of step (a) is selected from bromine, chlorine or iodine and said solvent of step (a) is selected from nitrobenzene, toluene or dimethyl formamide.

6. The process as claimed in claim 4, wherein said boronic acid of step (b) is selected from 4-(methoxycarbonyl)phenyl)boronic acid or 4-Methoxycarbonylphenylboronic acid pinacol ester.

7. The process as claimed in claim 4, wherein said palladium catalyst of step (b) is selected from tetrakis (triphenylphosphine) palladium or Palladium(II) acetate; said solvent of step (b) is selected from dioxane, tetrahydrofuran or toluene; and said base of step (b) is selected from potassium tribasic phosphate, potassium carbonate, potassium acetate or sodium carbonate.

8. The process as claimed in claim 4, wherein said base of step (c) is selected from sodium hydroxide, potassium hydroxide or lithium hydroxide and the solvent of step (c) is selected from tetrahydrofuran, dioxane, water or mixture thereof.

9. The process as claimed in claim 4, wherein said solvent of step (e) is selected from polyphosphoric acid; dioxane, tetrahydrofuran, toluene or a mixture thereof and the catalyst of step (e) is polyphosphoric acid.

10. A device comprising the two dimensional polymer of Formula (I) as claimed in claim 1, wherein said polymer of formula (I) is selected from BIP-1, BIP-2 or BIP-3.

* * * * *